(12) United States Patent
Miller et al.

(10) Patent No.: US 11,858,695 B2
(45) Date of Patent: Jan. 2, 2024

(54) LID CONSTRUCTION FOR BREATHING APPARATUS

(71) Applicant: Fisher & Paykel Healthcare Limited, Auckland (NZ)

(72) Inventors: Jeremy Livingston Miller, Auckland (NZ); Arjen David Kat, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/146,719

(22) Filed: Dec. 27, 2022

(65) Prior Publication Data

US 2023/0227216 A1    Jul. 20, 2023

Related U.S. Application Data

(63) Continuation of application No. 17/842,154, filed on Jun. 16, 2022, now Pat. No. 11,565,856, which is a continuation of application No. 16/929,662, filed on Jul. 15, 2020, now Pat. No. 11,390,430, which is a continuation of application No. 16/280,753, filed on
(Continued)

(51) Int. Cl.
*B65D 43/16* (2006.01)
*A61M 16/16* (2006.01)
*E05B 65/52* (2006.01)
*B65D 43/26* (2006.01)
(Continued)

(52) U.S. Cl.
CPC ........... *B65D 43/166* (2013.01); *A61M 16/16* (2013.01); *B65D 43/26* (2013.01); *E05B 65/52* (2013.01); *A61M 16/162* (2013.01); *A61M 2209/06* (2013.01); *E05D 3/022* (2013.01); *E05D 7/1066* (2013.01); *E05Y 2900/602* (2013.01); *Y10T 29/4984* (2015.01); *Y10T 292/57* (2015.04)

(58) Field of Classification Search
CPC ...... B65D 43/166; B65D 43/26; B65D 43/22; B65D 43/14; B65D 43/164; Y10T 29/4984; Y10T 292/57; A61M 16/16; A61M 16/162; A61M 2209/06; E05B 65/52; E05D 3/022; E05D 7/1066; E05D 2900/602
USPC .................. 220/264, 811, 815, 827, 263, 326
See application file for complete search history.

(56) References Cited

U.S. PATENT DOCUMENTS 4,196,725 A    4/1980    Gunderson
4,253,568 A    3/1981    Long et al.
(Continued)

FOREIGN PATENT DOCUMENTS

CN    101947343    1/2011
DE    2748185    5/1979
(Continued)

OTHER PUBLICATIONS

Nov. 25, 2013 Search Report and Written Opinion for PCT Application No. PCT/NZ2013/000175 Filed Sep. 23, 2013.
(Continued)

*Primary Examiner* — J. Gregory Pickett
*Assistant Examiner* — Niki M Eloshway
(74) *Attorney, Agent, or Firm* — Knobbe, Martens, Olson & Bear, LLP

(57) ABSTRACT

A breathing assistance apparatus has a lid and latch assembly configured for one-handed operation. The apparatus also includes a hinge assembly that separates when over-rotated but that reengages upon closing of the lid onto the main body of the apparatus.

14 Claims, 11 Drawing Sheets

Related U.S. Application Data

Feb. 20, 2019, now Pat. No. 10,752,409, which is a continuation of application No. 15/405,847, filed on Jan. 13, 2017, now Pat. No. 10,252,837, which is a continuation of application No. 14/667,499, filed on Mar. 24, 2015, now Pat. No. 9,546,025, which is a continuation of application No. PCT/NZ2013/000175, filed on Sep. 23, 2013.

(60) Provisional application No. 61/705,340, filed on Sep. 25, 2012.

(51) Int. Cl.
   *E05D 3/02* (2006.01)
   *E05D 7/10* (2006.01)

(56) References Cited

U.S. PATENT DOCUMENTS

| | | |
|---|---|---|
| RE30,890 E | 3/1982 | Hodge |
| 4,496,050 A | 1/1985 | Kirchner et al. |
| 4,741,433 A | 5/1988 | Irvine |
| 4,821,751 A | 4/1989 | Chen |
| 4,836,394 A | 6/1989 | Glomski |
| 4,867,302 A | 9/1989 | Takahashi |
| 4,887,747 A | 12/1989 | Ostrowsky et al. |
| 4,940,049 A | 7/1990 | Kirchgeorg et al. |
| 4,967,924 A | 11/1990 | Murofushi |
| 5,048,715 A | 9/1991 | Wolff |
| 5,078,297 A | 1/1992 | Howard |
| 5,078,397 A | 1/1992 | Aizawa |
| 5,150,806 A | 9/1992 | Glomski |
| 5,238,138 A | 8/1993 | Bois |
| 5,356,027 A | 10/1994 | Craft |
| 5,419,450 A | 5/1995 | Guglielmelli et al. |
| 5,430,248 A | 7/1995 | Levy |
| 5,520,313 A | 5/1996 | Toshihide |
| 5,887,744 A | 3/1999 | Mejas |
| 5,975,346 A | 11/1999 | Imperato |
| 6,000,550 A | 12/1999 | Simpson |
| 7,984,823 B2 | 7/2011 | Peng et al. |
| 8,006,691 B2 | 8/2011 | Kenyon |
| 8,206,058 B2 | 6/2012 | Vrondran et al. |
| 8,292,101 B1 | 10/2012 | Bragg |
| 8,476,540 B2 | 7/2013 | Dahl |
| 8,550,275 B2 | 10/2013 | Fuehrer |
| 9,546,025 B2 | 1/2017 | Miller et al. |
| 10,252,837 B2 | 4/2019 | Miller et al. |
| 10,752,409 B2 | 8/2020 | Miller et al. |
| 2001/0052524 A1 | 12/2001 | Ichimaru et al. |
| 2006/0091145 A1 | 5/2006 | Miller et al. |
| 2006/0191948 A1 | 8/2006 | Wisniewski |
| 2008/0302361 A1 | 12/2008 | Snow et al. |
| 2010/0012673 A1 | 1/2010 | McKeen |
| 2011/0052524 A1 | 3/2011 | de Vries et al. |
| 2011/0309098 A1 | 12/2011 | Hayashi et al. |
| 2012/0199513 A1 | 8/2012 | Wagner |
| 2017/0121067 A1 | 5/2017 | Miller et al. |
| 2021/0002038 A1 | 1/2021 | Miller et al. |

FOREIGN PATENT DOCUMENTS

| | | |
|---|---|---|
| GB | 2235682 | 3/1991 |
| GB | 2441796 | 1/2011 |
| JP | S51-6322 | 2/1976 |
| JP | S58-137773 | 9/1983 |
| JP | S60-47241 | 4/1985 |
| JP | 1992017622 | 2/1992 |
| JP | 07-71160 | 3/1995 |
| JP | 2000-055419 | 2/2000 |
| JP | 2000-070138 | 3/2000 |
| JP | 3-300267 | 7/2002 |
| JP | 2003-220580 | 8/2003 |
| JP | 3141547 | 5/2008 |
| JP | 2010-270966 | 12/2010 |
| JP | 2010-058957 | 12/2012 |

OTHER PUBLICATIONS

Australian Examination Report issued in AU Patent Application 2018204299, dated Dec. 4, 2018, in 4 pages.

Great Britian Examination Report issued in GB Patent Application GB1504950.5, dated Feb. 7, 2020 in 3 pages.

Chinese Office Action issued in CN Patent Application 201710567849, dated Jan. 15, 2020, in 11 pages.

LID CONSTRUCTION FOR BREATHING APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application is a continuation of U.S. application Ser. No. 17/842,154, filed Jun. 16, 2022, which is a continuation of U.S. application Ser. No. 16/929,662, filed Jul. 15, 2020, which is a continuation of U.S. Application No. 16,280,753, filed Feb. 20, 2019, which is a continuation of U.S. application Ser. No. 15/405,847, filed Jan. 13, 2017, which is a continuation of U.S. application Ser. No. 14/667,499, now U.S. Pat. No. 9,546,025, filed Mar. 24, 2015, which is a continuation of PCT International Application No. PCT/NZ2013/000175, filed Sep. 23, 2013, which claims priority to U.S. Provisional Application No. 61/705,340, filed Sep. 25, 2012, the entirety of each of which is hereby incorporated by reference herein.

BACKGROUND OF THE INVENTION

Field of the Invention

The present invention generally relates to respiratory devices. More particularly, the present invention relates to respiratory devices in which respiratory gases are supplied at a positive pressure after passing over a surface of liquid in a reservoir.

Description of the Related Art

CPAP treatment of obstructive sleep apnea involves the delivery of pressurized, breathable gas, usually air, to a user's airways using a conduit and a user interface, such as a mask. The gas pressures employed for CPAP typically range from about 4 cm H2O to about 28 cm H2O at flow rates of up to about 180 L/min (measured at the user interface), depend upon the requirements of the user. The pressurized gas acts as a pneumatic splint for the airway of the user. As such, the pressurized gas reduces the likelihood of collapsing of the airway.

SUMMARY OF THE INVENTION

CPAP machines include an airflow generator to supply the pressurized gas and many CPAP machines include a heated water bath or other source of water for humidification of the pressurized gas. CPAP machines often are used in bedrooms or other sleeping quarters and are placed on nightstands, for example. As such, reducing the footprint of CPAP machines is desirable. In addition, given the limited space of nightstand tops, CPAP machines often are pushed as close to a wall as possible.

Because of the cramped spaces in which CPAP machines are used, easy manipulation of a lid or other component used to enclose a water reservoir or the like is desired. Preferably, the lid or such component can be easily pivoted about hinges. More preferably, the hinges are configured to be generally flush with, or recessed into, the adjoining outer surfaces. Even more preferably, the hinges provide a restraint against forces generated by air pressure within the machine (e.g., vertical forces with a generally horizontal lid) while allowing detachment of the lid when the lid is over-extended during opening.

Moreover, to improve the ability to access the water reservoir, the lid preferably carries a latch mechanism such that a user can open the lid with a single hand. In other words, the latch can be operated and the lid can be opened with a single hand and, preferably, with the single hand in a single position. Such configurations are a welcomed improvement over configurations requiring one hand to operate the latch and another hand to subsequently raise the lid.

In some configurations, a breathing assistance apparatus comprises a lid and a main body with the lid and the main body selectively enclosing a cavity. The lid comprises a button member and at least one hinge assembly.

In some configurations, the lid further comprises a component adapted to be engaged with one or more fingertips while the button member is depressed.

In some configurations, the button member is spring biased away from the at least one hinge assembly.

In some configurations, the at least one hinge assembly allows pivotal movement of the lid relative to the main body.

In some configurations, the hinge assembly comprises at least one post and at least one support, the supports overlying the post and the post being positioned inboard of an outer perimeter of the lid.

Preferably, the hinge assembly comprises a clip extending along at least an axial length of the post, the clip being positioned on an opposite side of the post from the supports such that the post is captured between the clip and the supports.

In some configurations, the at least one hinge assembly comprises a guide structure and cam structure, the guide structure and the cam structure configured to cause sliding movement of the post during rotation of the post.

In some configurations, the guide structure comprises a guide surface, wherein in use the guide surface contacts the cam structure to move the lid from a detached state to an attached state relative to the main body via the sliding movement of the post as a result of closing motion of the lid.

Preferably, the sliding movement only occurs when the lid is moved from a disengage state to an engaged state with respect to the main body.

Preferably, the sliding movement of the post is substantially horizontal with the supports being positioned at least vertically above the post with the lid in the closed position.

In some configurations, the at least one support defines an opening that permits the at least one post to pass through the opening such that in use the lid can be moved from a detached state to an attached state relative to the main body.

In some configurations, a method of opening a lid of a breathing apparatus comprises moving a button member toward an engagement component to unlatch the lid and then rotating the lid to an opened position without the user having to reposition a hand.

In some configurations, a method of engaging a lid on a main body of a breathing apparatus comprises placing a post alongside at least one support member with the lid in an open position, pivoting the lid toward a closed position such that at least one engaging structures formed on the lid and at least one engaging structure formed on the main body cause the lid to translate into an engaged structure with the lid being pivotable while in the engaged structure.

BRIEF DESCRIPTION OF THE DRAWINGS

These and other features, aspects and advantages of the present invention will be described with reference to the following drawings.

DETAILED DESCRIPTION OF THE PREFERRED EMBODIMENTS

Figure 1:
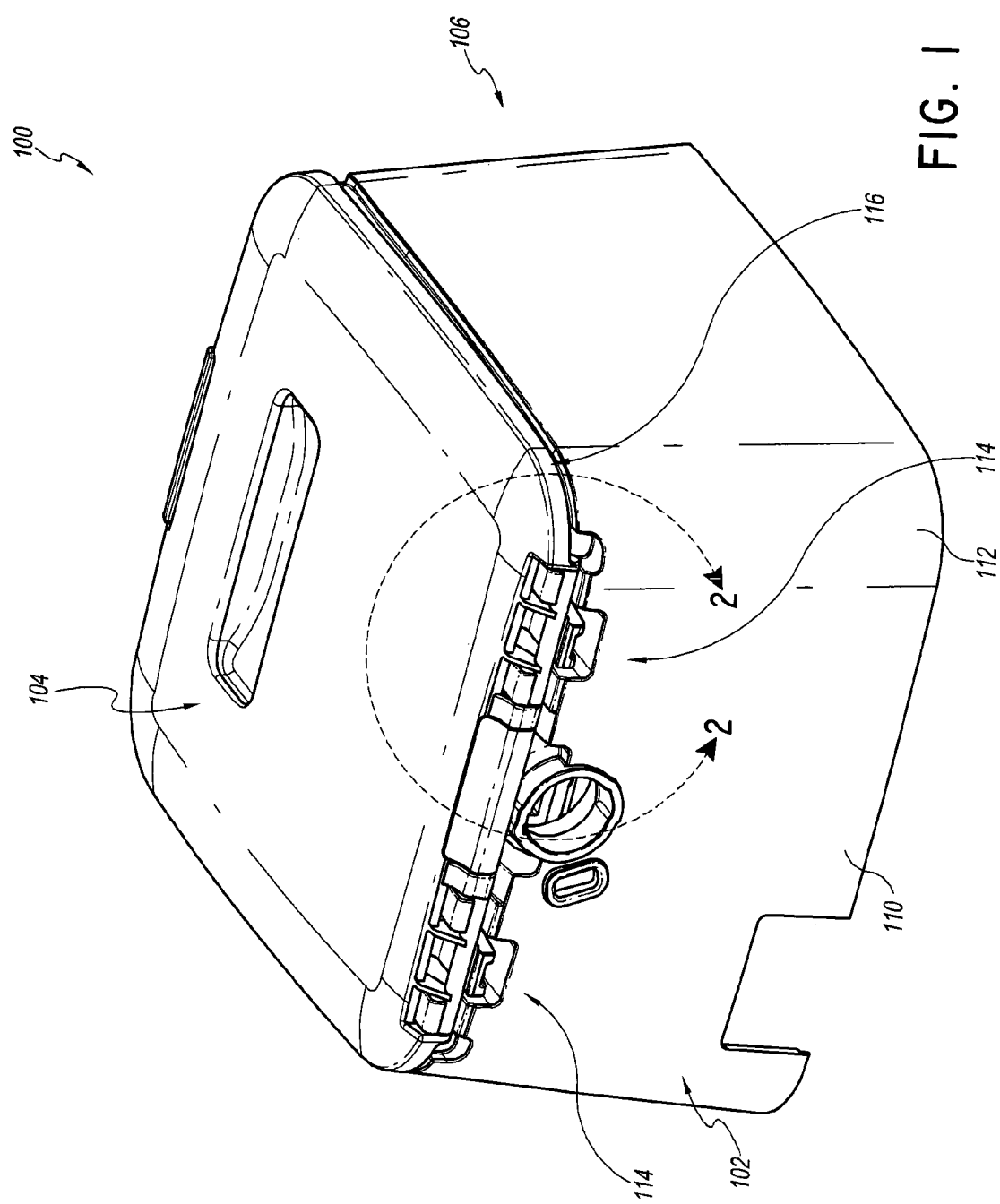
FIG. 1 is a rear perspective view of a breathing assistance apparatus that is arranged and configured in accordance with certain features, aspects and advantages of the present invention.

FIG. 1 illustrates a breathing assistance apparatus 100 that is arranged and configured in accordance with certain features, aspects and advantages of the present invention. The apparatus 100 comprises a main body 102 and a lid 104. Together, the main body 102 and the lid 104 define a housing 106 that encloses, or generally encases, a reservoir, tub, tank or other body of liquid (not shown) within a cavity.

The illustrated body 102 comprises at least one outer surface 110. In the illustrated configuration, the body 102 comprises four generally planar outer surfaces 110 that are connected by rounded corners 112. Other configurations are possible.

The lid 104 is connected to the body 102 with hinge assemblies 114. In the illustrated configuration, the lid 104 is connected to a rear of the main body 102 using two hinge assemblies. The lid 104 can be connected to other surfaces. In addition, the lid 104 can be connected to the main body 102 using as few as one hinge assembly 114 or more than two hinge assemblies 114. Preferably, the hinge assemblies 114 are constructed such that, with the lid 104 in the closed position (e.g., as shown in FIG. 1), the hinge assemblies 114 are generally flush with or recessed into the rear outer surface 110. In some configurations, the hinge assemblies 114 are constructed such that the hinge assemblies do not protrude rearward of the rear outer surface 110. In some configurations, some of the hinge features may protrude very slightly from one or more surrounding surface of the rear outer surface or other surrounding portion of the apparatus. In some configurations, the lid 104 comprises an outer perimeter 116 and the hinge assemblies 114 do not protrude significantly outward of the outer perimeter 116 of the lid 104.

Figure 2:
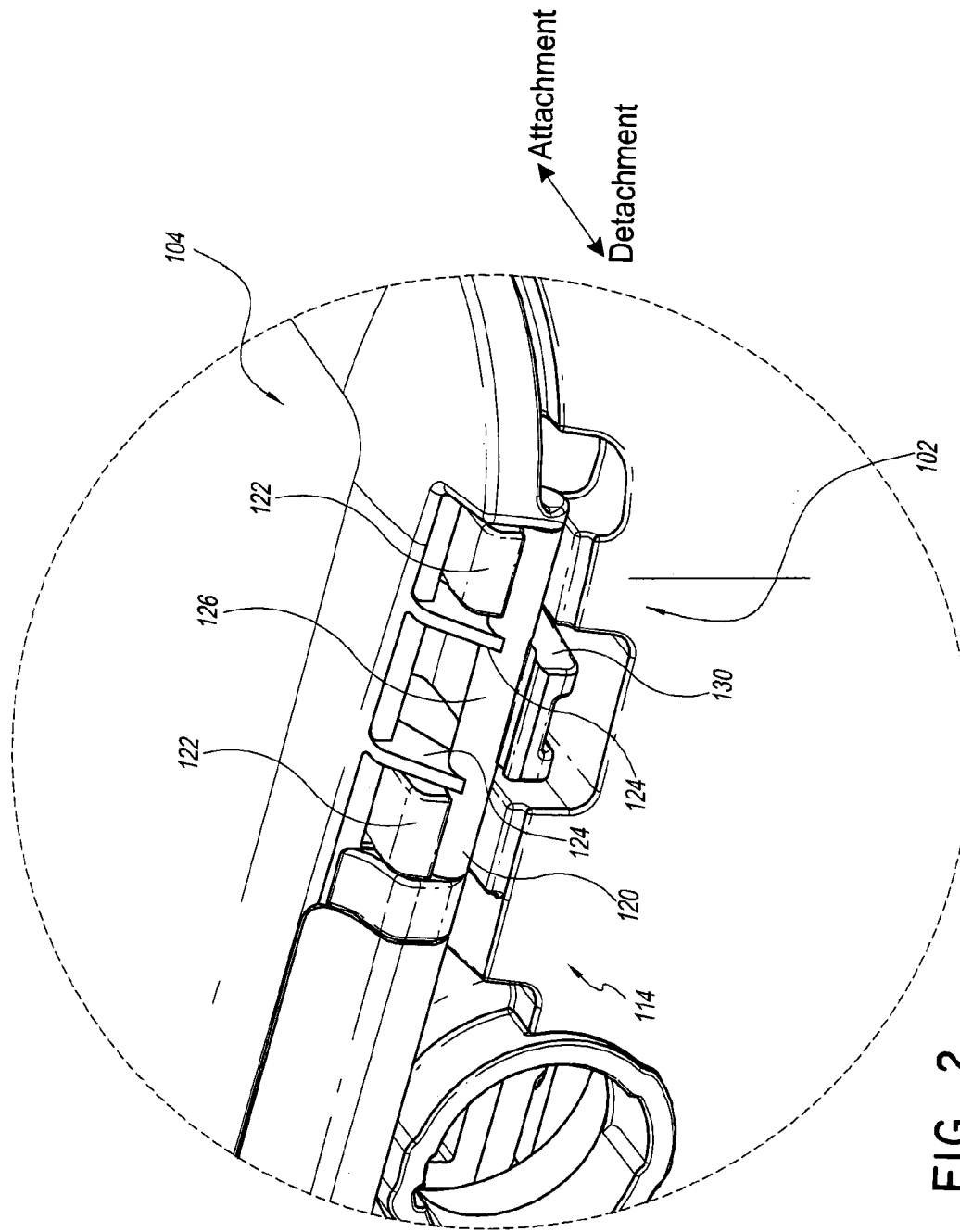
FIG. 2 is an enlarged rear top perspective view of a hinge of the breathing assistance apparatus of FIG. 1 with a lid in a closed position.

With reference to FIG. 2, the hinge assemblies 114 comprise at least one post 120 and at least one support 122. Preferably, the at least one post 120 is mounted such that the post is recessed and located inside of the outer perimeter 116 of the lid. The illustrated configuration comprises a single post 120 that is connected to two supports 122. In some configurations, the at least one post 120 is mounted to the lid 104 while the at least one support 122 is mounted to the main body 102. In some configurations, the at least one post 120 can be mounted to the main body 102 while the at least one support 122 can be mounted to the lid 104.

The at least one post 120 can be secured to the lid 104 using one or more standoffs 124. In the illustrated construction, the standoffs 124 are positioned between the two supports 122. The standoffs reduce the deflection of the post 120 in the region of the supports 122. In some configurations, the portion 126 of the post 120 extending between the standoffs 124 can be omitted. In the illustrated configuration, however, the portion 126 of the post 120 can be secured by a clip 130. The clip 130 can have a recess that accommodates the post 120 or any other suitable configuration.

A force generated by the clip 130 on the post 120 in the illustrated configuration is opposed by forces generated by the supports 122, for example. The clip 130 can contact an opposite side of the post 120 relative a contact region between the supports 122 and the post 120. In some configurations, the clip 130 can be configured to deflect away from the post 120 during assembly of the post 120 and the clip 130. For example, the clip 130 can be a deflectable finger that extends rearward from the main body 102. The supports 122 can have a recess that defines a rearwardly-opening mouth that receives at least a portion of a circumference of the post 120. Accordingly, movement of the post 120 in the directions shown by the arrow can result in attachment and detachment of the post 120 relative to the supports 122 and the clip 130. The rearwardly-opening mouth of the supports 122 also results in a structure that overlies the post 120 such that vertical movement of the post 120 relative to the supports 122 is not possible with the post 120 fully received within the mouths of the supports 122. As such, the lid 104 is unlikely to separate from the main body 102 during therapy.

Figure 3:
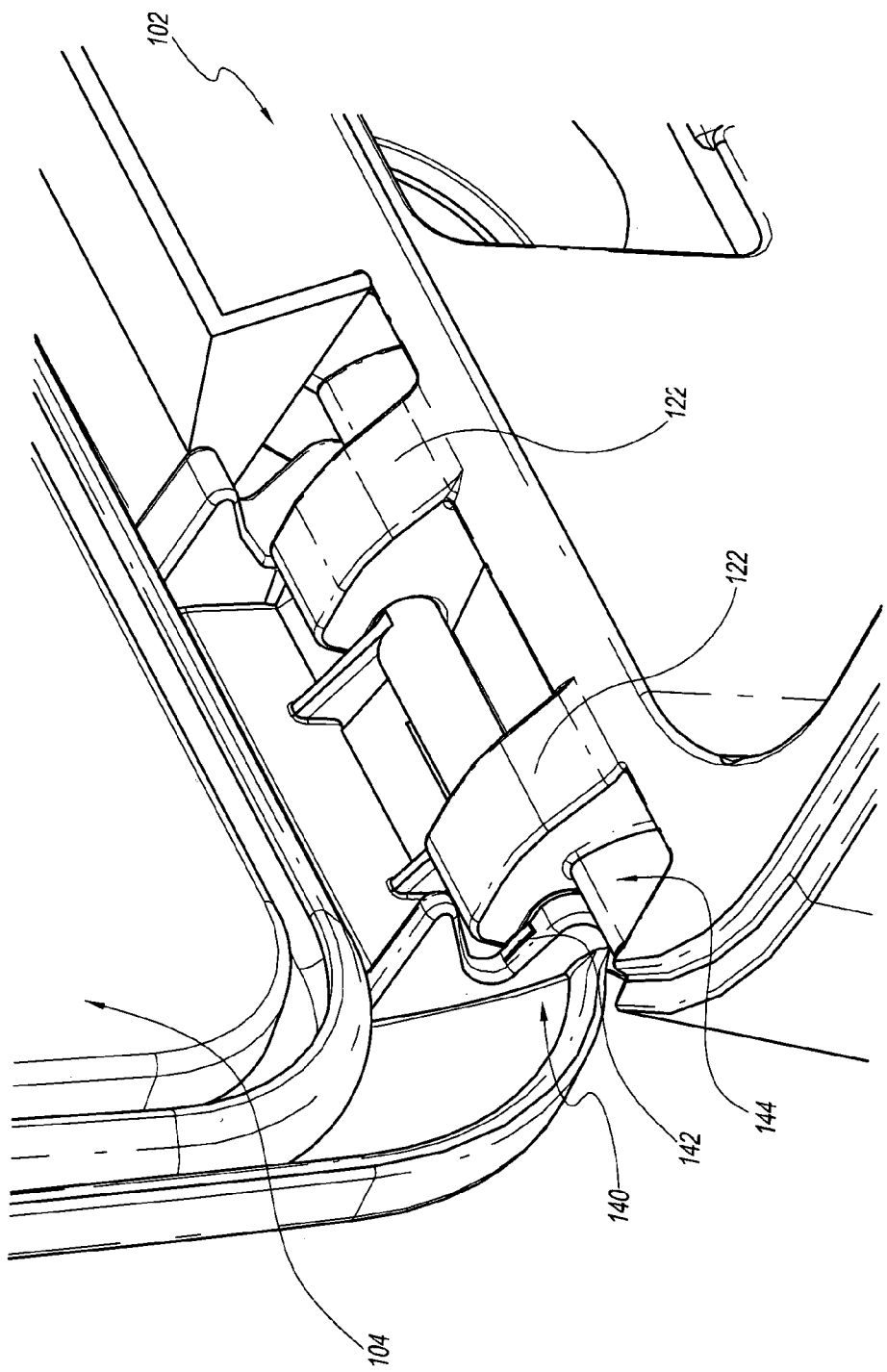
FIG. 3 is an enlarged front perspective view of the hinge of FIG. 2 showing the lid in an opened position.

With reference to FIG. 3, the lid 104 and the main body 102 can include structures that guide the post 120 and the clip 130 and supports 122 into connection. In some configurations, the structures facilitate movement of the at least one post 120 into the mouth of the supports 122 and into engagement with the clip 130 when the lid 104 is brought toward the closed position on the main body 102. In the illustrated configuration, two guide structures 140 are positioned outboard of the two supports 122. Other configurations also are possible.

Figure 4:
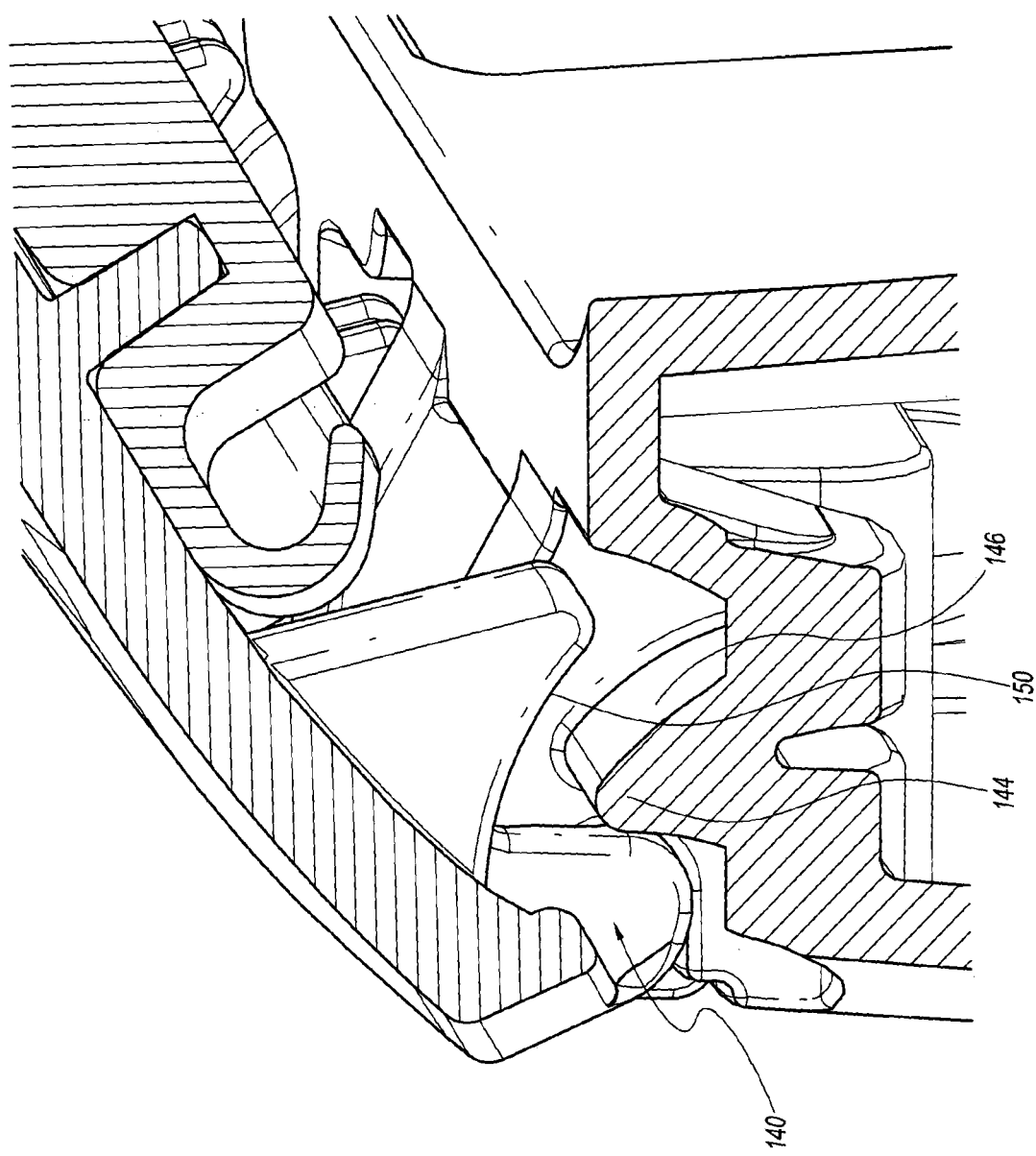
FIG. 4 is a sectioned perspective view of the hinge of FIG. 2 showing the lid in a partially closed position.

With reference to FIG. 4, the guide structure 140 comprises a recess 142 that receives a cam structure 144. The cam structure 144 is received within the recess 142 such that, with the lid 104 moved to the fully closed position on the main body 102, the cam structure 144 does not prevent the lid 104 from fully closing. The cam structure 144 tapers toward a point with a sloping surface 146 such that the thickness of the cam structure 144 increases from back to front while the guide structure has an opposing surface 150. The sloping surface 146 and the opposing surface 150 engage each other such that the sloping surface 146 and the opposing surface 150 resists movement of the lid 104 relative to the main body 102 in the detachment direction (see FIG. 2) when the lid 104 is in an at least partially closed position.

Moreover, as the lid 104 is rotated toward a closed position (e.g., FIG. 1), the sloping surface 146 and the opposing surface 150 act to draw the lid 104 forward into the attachment position (e.g., the at least one post 120 connected to the supports 122 and the clip 130). Thus, rotation of the lid 104 can result in the hinge assemblies 114 being operatively connected from a detached state. In some configurations, the difference in thicknesses of the sloping surface 146 and the opposing surface 150 from initial contact to fully closed is substantially the same as a distance from the outer surface of the post 120 and the first contact with the supports 122 such that as the sloping and opposing surfaces 146, 150 are moved into full engagement along their lengths, the post 120 is pulled into position within the supports 122 and the clip 130.

Notably, with the lid 104 in the open position (e.g., FIG. 3) relative to the main body 102, sufficient space exists between the sloping surface 146 and the opposing surface 150 such that the lid 104 can be separated from the main body 102 with the application of force. Advantageously, such a construction allows separation between the lid 104 and the main body 102 by disconnection of the posts 120 from the supports 122 and the clips 130. Such a separation can protect the apparatus 100 from damage resulting from forces that result from over-opening of the lid or from possible misuse of the apparatus 100. Accordingly, the ability to separate the lid 104 from the main body 102 can protect the apparatus 100 from permanent damage. As discussed above, the lid 104 can be easily reconnected by placing the posts 120 alongside the supports 122 and rotating the lid 104 toward a closed position, which results in the sloping surface 146 of the cam structure 144 and the opposing surface 150 of the guide structure drawing the components back together.

Figure 5:
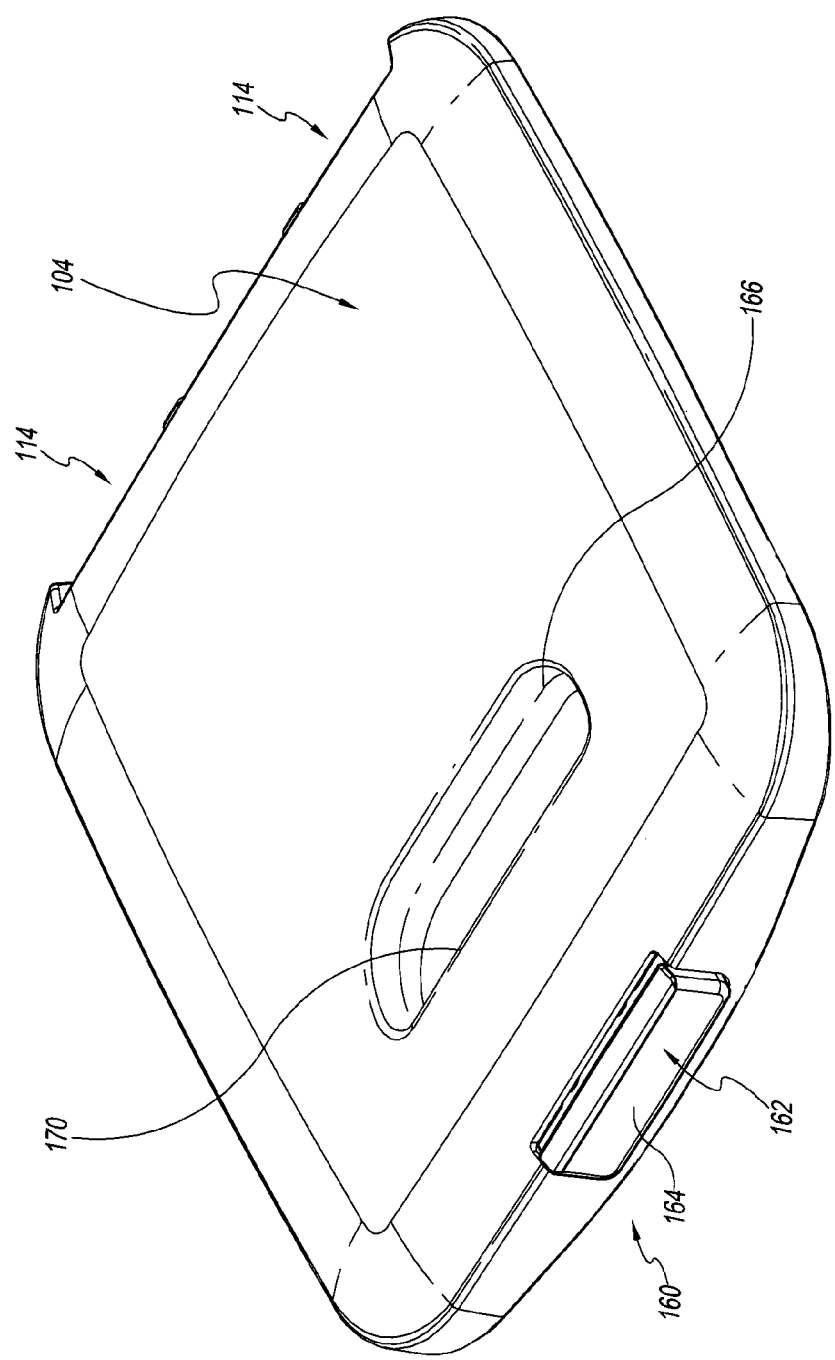
FIG. 5 is a front perspective view of the lid of the breathing assistance apparatus of FIG. 1, which lid is arranged and configured in accordance with certain features, aspects and advantages of the present invention.

With reference now to FIG. 5, a release and handle assembly 160 of the lid 104 will be described. As illustrated, the release and handle assembly 160 comprises at least one button member 162 that is mounted on the lid 104. In some configurations, the button member 162 is mounted for movement toward and away from the hinge assemblies 162. In some configurations, the button member 162 can be mounted along a side of the lid 104 that is adjacent to the side of the lid 104 having the hinge assemblies 162. In the illustrated configuration, the button member 162 is mounted on an opposing side of the lid 104 relative to the hinge assemblies 114 and capable of movement toward and away from the hinge assemblies 114.

Figure 6:
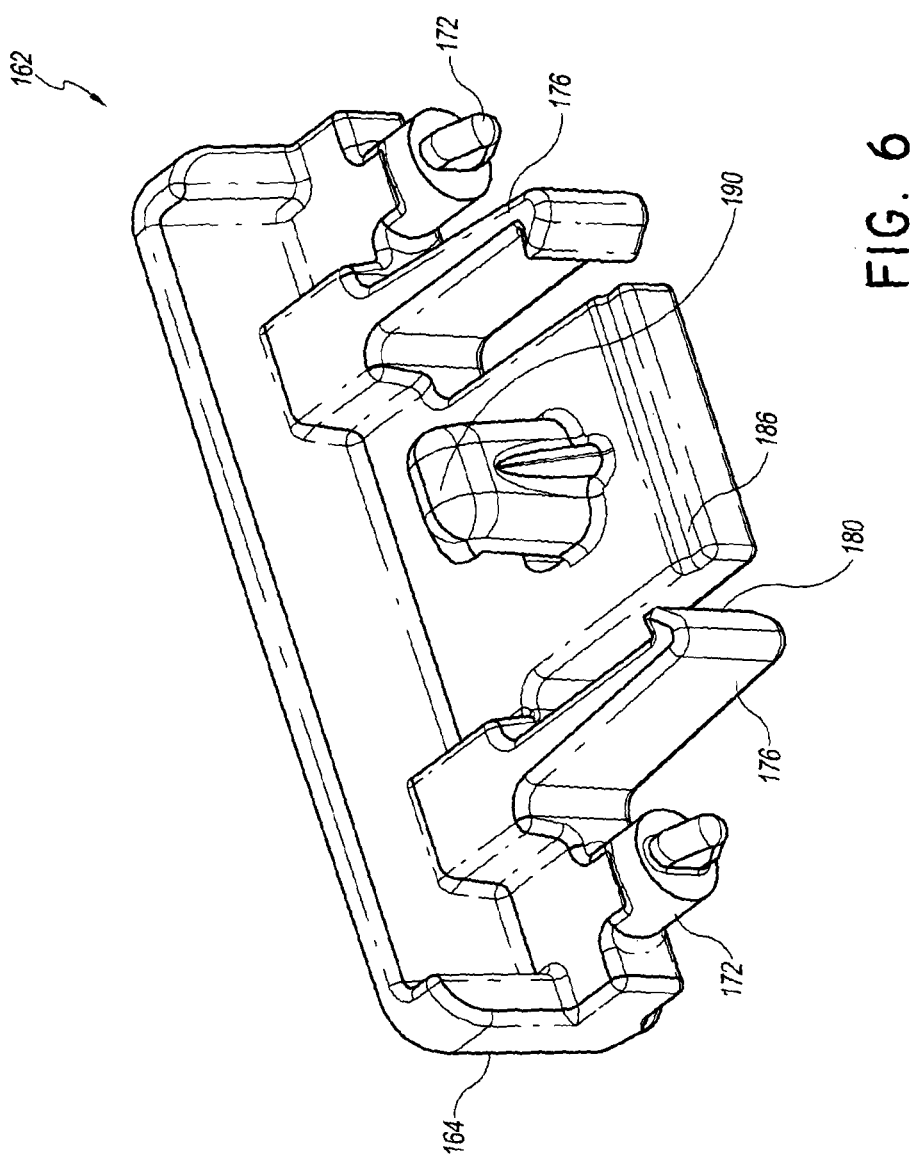
FIG. 6 is a rear bottom perspective view of a latch member of the lid of FIG. 5.

The button member 162 is illustrated in FIG. 6. The button member comprises an exterior surface 164, which is best shown in FIG. 5. The exterior surface 164 is sufficiently large for contact with a finger or thumb. As also illustrated in FIG. 5, the lid 104 can comprise a component 166 that is used to raise the lid 104. In the illustrated configuration, the component 166 is a recessed region that has a wall 170 extending generally parallel with the exterior surface 164. Preferably, the recessed region 166 is sufficiently large as to accommodate at least tips of fingers. In some configurations, the component 166 is one or more lip, ridge, protrusion, recess or the like. Accordingly, the component 166 (e.g., having the wall 170) and the exterior surface 164 can allow a simple squeezing action to accomplish both an unlatching of the button member 162 as well as providing a grasping action to allow movement of the lid 104 away from the main body 102.

With reference again to FIG. 6, the illustrated button member 162 comprises two outer posts 172. The posts 172 are sized and configured to engage with biasing members, such as compression springs or the like, for example but without limitation. The posts 172 are received within corresponding housings 174 that are formed in the lid 104. The housings 174 can contain the biasing members and the posts 172 can slide into and out of the housings 174 against the biasing force of the biasing members.

Figure 7:
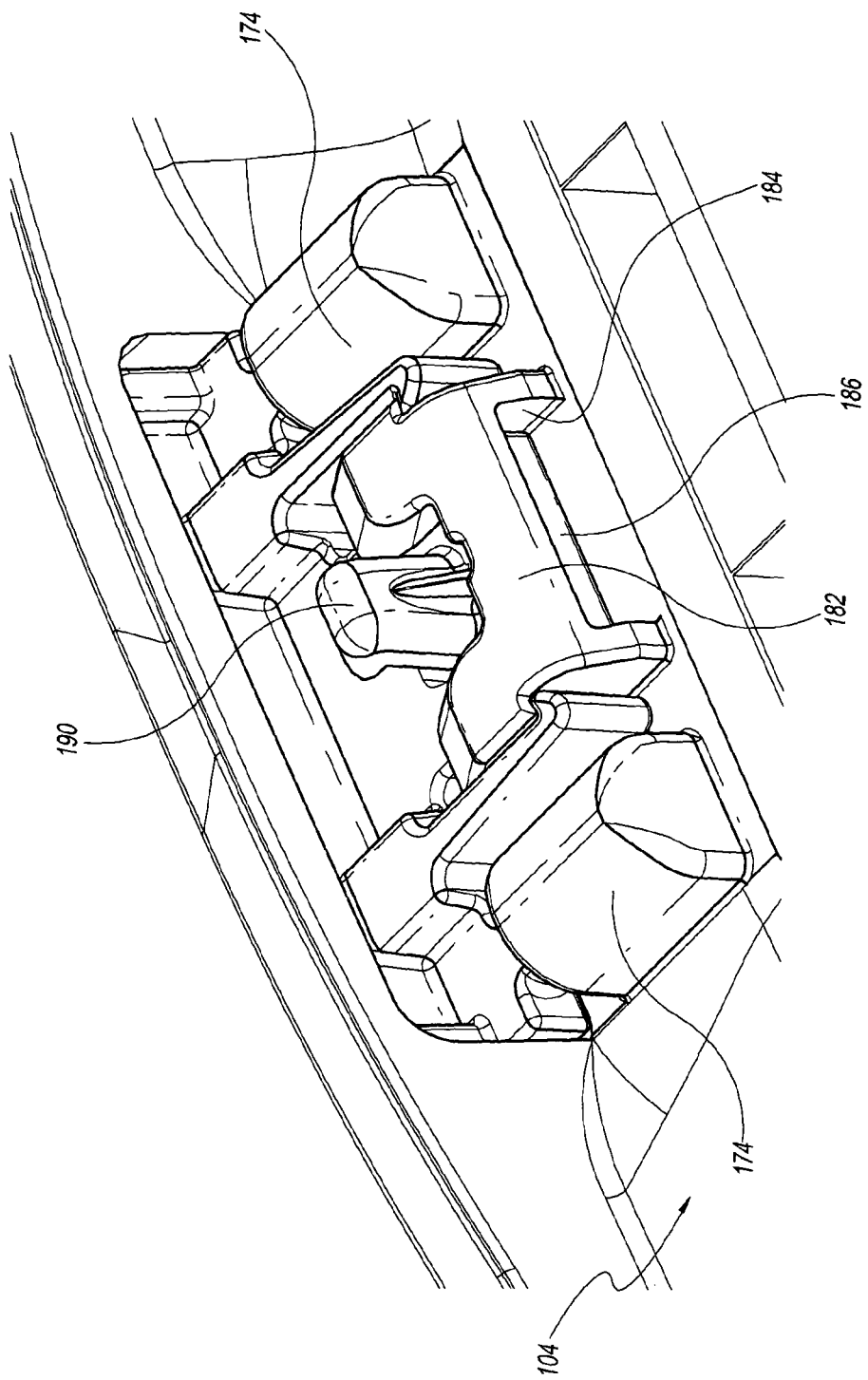
FIG. 7 is a rear bottom perspective view of the latch member of FIG. 6 shown assembled to the lid.

The illustrated button member 162 also comprises at least one tab 176. In the illustrated configuration, the button member 162 comprises two tabs 176. The tabs 176 are bayonet shaped with a barb 180 at the end. As shown in FIG. 7, the tabs 176 can engage a structure 182 formed in the lid 104. Thus, the tabs 176 in cooperation with the structure reduce the likelihood of the button member 162 coming out of a recess of the lid 104 while allowing inward depression of the button member 162 relative to the lid 104.

The structure 182 also comprises a passage 184 that receives a finger 186 mounted to, or formed on, the button member 162. The passage 184 facilitates generally only linear translation of the button member 162 relative to the lid 104. In other words, the passage 184 receives the finger 186 and the finger 186 is generally limited by the passage 184 to substantially linear movement.

The finger 186 supports a locking post 190. The locking post 190 can engage with a structure formed on the main body 102. In some configurations, the locking post 190 engages with a structure formed on an inner surface of the main body 102 such that the depression of the button member 162 results in separation between the locking post 190 and the structure with which it normally engages. Releasing of the button member 162 results in the biasing members moving the locking post 190 into position for reengagement with the structure with which it normally engages.

Figure 8A:
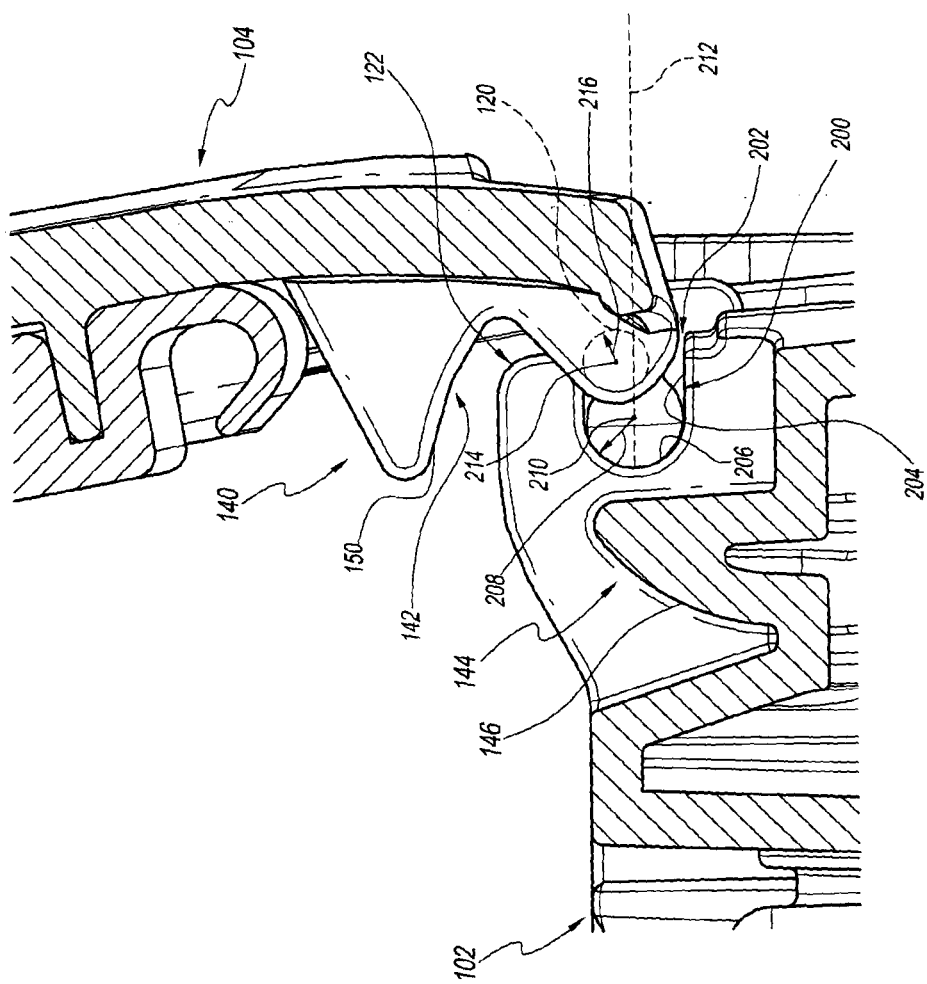
FIGS. 8A-8D are side views of a guide structure of the hinge of FIG. 2 in several positions from opened to closed.
Figure 8B:
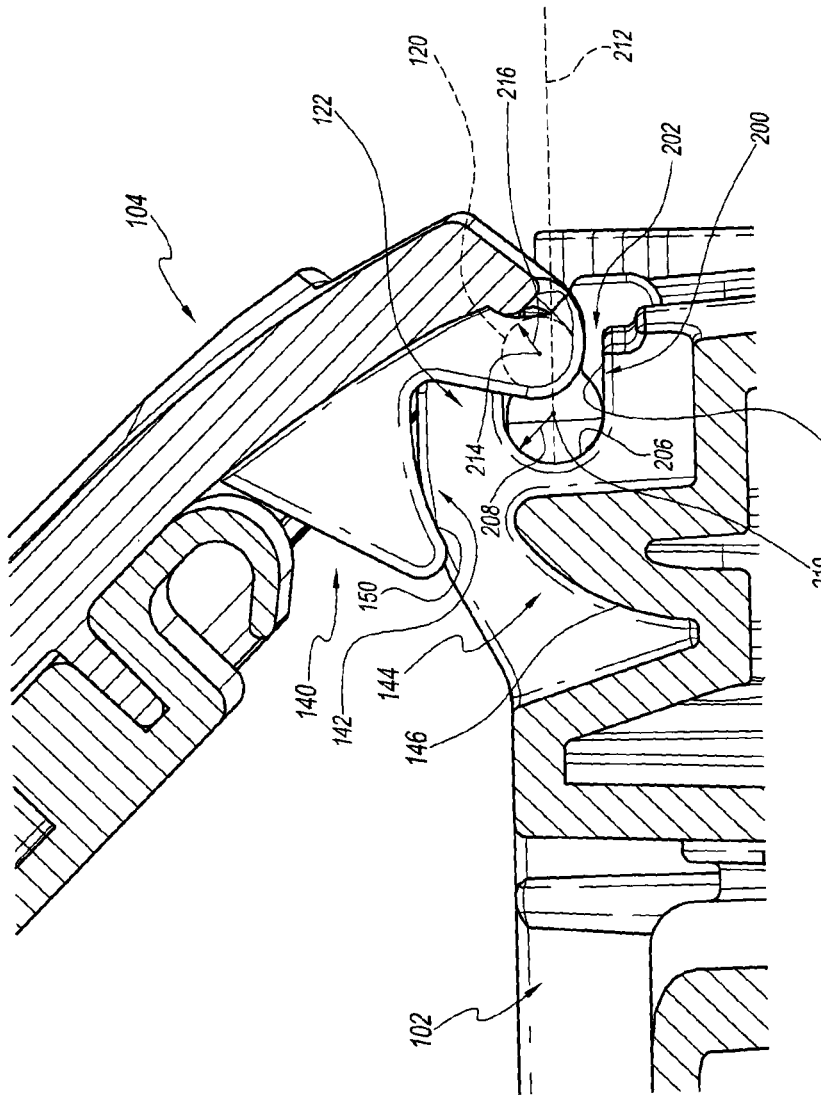
Figure 8C:
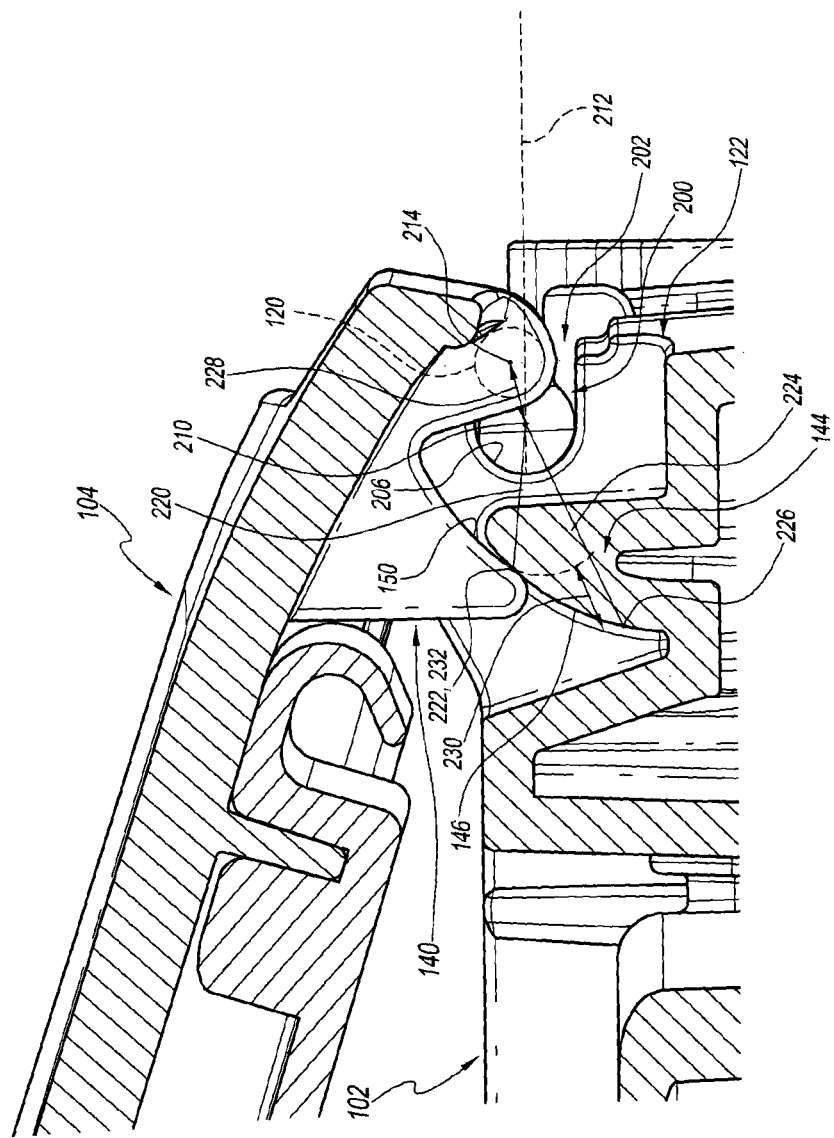
Figure 8D:
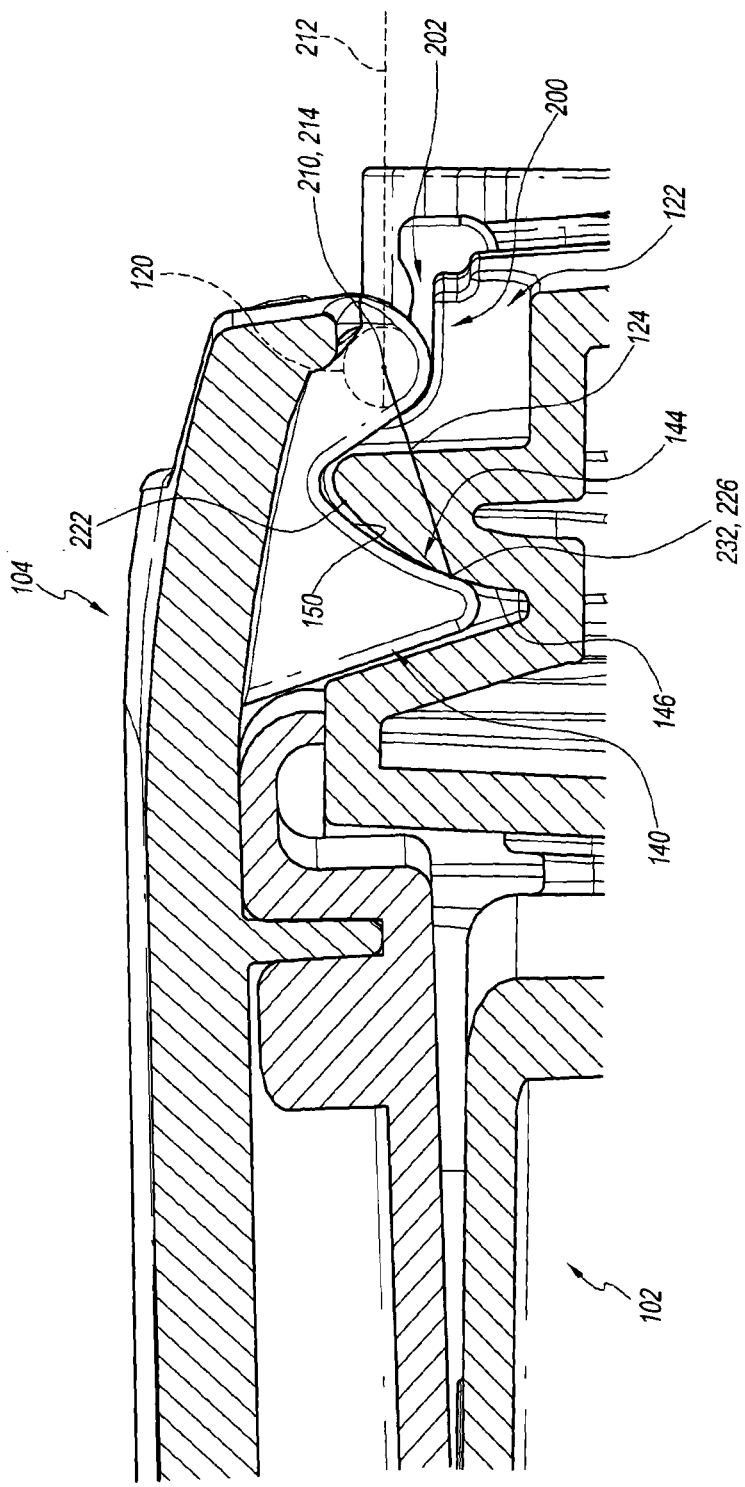

FIGS. 8A-8D illustrate the lid 104 in several positions relative to the main body 102. FIG. 8A illustrates the lid 104 in a first opened position. FIGS. 8B and 8C illustrate the lid 104 in progressively further closed positions relative to the first opened position of FIG. 8A. FIG. 8D illustrates the lid 104 in a closed position. In particular, FIGS. 8A-8D further illustrate the interaction between the sloping surface, or cam surface, 146 of the cam structure 144 and the opposing surface (also referred to as a guide surface or cam follower surface) 150 of the lid recess 142 as the lid 104 moves from an opened position to a closed position. As described herein, the cam structure 144 and the recess 142 can interact to move the lid 104 from a detached position relative to the main body 102 to an attached position relative to the main body 102 when the lid 104 is moved from an opened position to a closed position.

As described herein, the support 122 includes the recess 200 comprising the mouth 202, which opens in a rearward direction in the illustrated arrangement. Preferably, the recess 200 is elongate in shape and extends in a generally fore-aft direction. In the illustrated arrangement, the recess 200 is generally or substantially horizontal or aligned with a bottom support surface of the main body 102 such that the recess 200 is generally or substantially horizontal when the apparatus 100 is rested on a flat surface. The recess 200 includes upper and lower guide surfaces 204 that extend forwardly from the mouth 202 to an end surface 206. As described herein, the support 122 also assists in retaining the lid 104 on the main body 102 in response to forces within the housing 106 (e.g., forces resulting from internal pressure) tending to separate the lid 104 from the main body 102. Thus, the upper portion of the end surface 206 and/or the upper guide surface 204 can form a retention surface that contacts the post 120 to retain the lid 104, or at least a portion of the lid 104 near the support 122 and/or hinge 114 (e.g., a rearward portion), on the main body 102 in response to forces tending to separate the lid 104 from the main body 102.

In the illustrated arrangement, the end surface 206 is curved (e.g., semi-circular) in shape from a side view and connects the upper guide surface 204 and the lower guide surface 204. The illustrated support 122 is elongate in a lateral or side-to-side direction and, thus, defines a substantially semi-cylindrical shape in three dimensions. However, for convenience, the hinge 114, guide structure 140 and cam structure 144 may be described herein in the context of the side views of FIGS. 8A-8D in two-dimensional terms. It will be appreciated that the described structures also have a width dimension relative to the apparatus 100 or a depth dimension relative to the side view of FIGS. 8A-8D.

The illustrated end surface 206 is defined by a curve having a radius 208 from a center point 210 (or an axis in three dimensions). The recess 200 can have a longitudinal axis 212 that extends along a length of the recess 200 generally from the mouth 202 to the end surface 206 and, in the illustrated configuration, passes through the center point 210. The axis 212 can be aligned with or parallel to one or both of the upper and lower guide surfaces 204 or can be centrally-located between the guide surfaces 204 (such as in the event of a tapered recess, for example and without limitation). In the illustrated configuration, the axis 212 is generally or substantially horizontal (or parallel to a bottom surface of the main body 102). However, in other configurations, the axis 212 could be non-horizontal or angled relative to the bottom surface of the main body 102).

As described herein, the post 120 preferably is cylindrical in shape or circular in shape from a side view, as illustrated in FIGS. 8A-8D. The post 120 defines a center point 214 (or an axis in three dimensions) and a radius 216. Preferably, the radius 216 of the post 120 is substantially equal to the radius 208 of the end surface 206 such that the post 120 can be snugly positioned against the end surface 206 and restrained in a vertical direction within recess 200 with the center points 210, 214 substantially aligned or coaxial with one another.

Preferably, the cam surface or sloping surface 146 of the cam structure 144 is positioned or oriented relative to the end surface 206 and/or center point 210 such that the post 120 is moved along the axis 212 of the recess 200 toward the end surface 206 as the lid 104 is moved from the opened toward the closed position. In the illustrated arrangement, a first distance 220 is defined between a first point or location 222 on the sloping surface 146 and the center point 210 and a second distance 224 is defined between a second point or location 226 on the sloping surface 146 and the center point 210. Preferably, the first point 222 is located on an initial portion of the sloping surface 146 and the second point 226 is located on a subsequent portion of the sloping surface 146 such that the opposing surface 150 will contact the first point 222 before the second point 226 as the lid 104 is moved from an opened position to a closed position. The first point 222 can be at or near the location that is first contacted by the opposing surface 150 during closing of the lid 104 and the second point 226 can be at or near the furthest location along the sloping surface 146 contacted by the opposing surface 150 when the lid 104 is in the closed position. The first distance 220 preferably is smaller than the second distance 224, which causes the movement of the post 120 along the axis 212 of the recess 200 as the lid 104 is moved from an opened position to a closed position and the opposing surface 150 moves along the sloping surface 146 in a direction from the first point 222 towards the second point 226.

A distance 228 traveled by the center point 214 of the post 120 within the recess 200 when the lid 104 is closed preferably is substantially equal to a difference 230 between the second distance 224 and the first distance 220. The distance 228 can be less than an overall length of the recess 200 because the post 120 can be at least partially located within the recess 200 prior to being drawn to the end surface 206 by the guide structure 140. In other arrangements, the distance 228 could be substantially equal to a length of the recess 200. Although the distances described immediately above are in relation to the center points 210 and 214, the distances similarly could be measured relative to other points on locations on the recess 200 (e.g., end surface 206) and post 120, respectively, if desired, such as in the context of non-circular (or non-cylindrical) recess or post shapes.

FIG. 8A illustrates the lid 104 in a first open position relative to the main body 102, which may be a fully opened position, such as when initiating a process of reattachment of the lid 104. As illustrated, the opposing surface 150 is clear of the sloping surface 146 such that rearward movement (e.g., detachment) of the lid 104 is permitted. Advantageously, such an arrangement reduces the likelihood of permanent damage resulting from excessive opening forces applied to the lid 104. FIG. 8B illustrates the lid 104 in a second open position that is further towards a closed position relative to the first open position of FIG. 8A. In FIG. 8B, the opposing surface 150 remains clear of the sloping surface 146. That is, a vertical gap exists between a bottom of the opposing surface 150 and a top of the sloping surface 146.

FIG. 8C illustrates the lid 104 in a third open position that is further towards a closed position relative to the positions of FIGS. 8A and 8B. In the position of FIG. 8C, a leading portion or engagement portion 232 of the opposing surface 150 is engaged with or contacts an initial portion of the sloping surface 146, which may be at or near the first point or location 222. In the illustrated arrangement, the post 120 is spaced away from the end surface 206 of the recess 200. FIG. 8D illustrates the lid 104 in a position that is further towards a closed position than the positions of FIGS. 8A-8C. The position of FIG. 8D can be a fully closed position of the lid 104. In the illustrated arrangement, at least the leading portion or engagement portion 232 of the opposing surface 150 is engaged with or contacts a subsequent portion of the sloping surface 146 spaced from the initial portion. The subsequent portion may be at or near the second point or location 226. Preferably, the post 120 is snugly positioned against the end surface 206 in the position of FIG. 8D. Thus, preferably, a distance between the engagement surface 232 and the center point 214 is preferably substantially equal to the second distance 224.

As described herein, the interaction of the guide structure 140 and the cam structure 144 as illustrated in FIGS. 8A-8D may occur only during a reattachment or engagement procedure for the lid 104. In normal opening and closing movement, sliding of the post 120 (or significant sliding of the post 120) within the recess 200 may not occur. Advantageously, such an arrangement reduces wear by reducing the amount of sliding movement between components during normal use. However, other arrangements are possible in which the sliding movement of the post 120 occurs more often than only during engagement of the lid 104, such as during normal opening and closing of the lid 104.

Although the illustrated opposing surface 150 has a similar size and shape as the sloping surface 146 and extends along a substantial portion of the sloping surface 146 when the lid 104 is in the closed position, other arrangements are also possible. For example, the opposing surface 150 could be a smaller surface, such as a cam follower surface, defining an engagement portion 232 that contacts only a point or small length of the sloping surface 146 in any one position. The engagement portion 232 could be rotatable such that it rolls along the sloping surface 146, if desired. Moreover, as disclosed herein, the illustrated arrangements could be reversed such that the cam surface or sloping surface 146 is carried by the lid 104 and the opposing surface 150 (or cam follower with engagement portion 232) is carried by the main body 102.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

What is claimed is:

1. A breathing assistance apparatus comprising:
   a main body comprising a cavity;
   a lid rotatable between an opened position and a closed position, the lid enclosing the cavity when in the closed position;
   at least one of the lid and the main body comprising a post, and another of the lid and the main body comprising a corresponding support, the support comprising a recess, the recess being able to receive at least a portion of the post, the recess comprising a mouth and an end surface, the end surface being forward of the mouth, the recess comprising an axis, the axis being defined between the mouth and the end surface, the mouth receiving the post when the lid is in a detached open position;
   at least one of the lid and the main body comprising a cam structure, and another of the lid and the main body comprising a guide structure, the cam structure comprising a first contact point and a second contact point, a sloping surface extending between the first contact point and the second contact point, the cam structure being able to contact the guide structure along the sloping surface as the lid is rotated from the detached open position to an attached closed position; and
   the first contact point and the second contact point of the cam structure being separated by a first distance that is parallel to the axis of the recess, the first distance being equal to a second distance, the second distance corresponding to a distance moved by the post along the axis during attachment of the lid to the main body.

2. The breathing assistance apparatus of claim 1, wherein the cam structure is able to contact the guide structure from the first contact point to the second contact point.

3. The breathing assistance apparatus of claim 1, wherein the axis of the recess is non-horizontal relative to a bottom surface of the main body.

4. The breathing assistance apparatus of claim 3, wherein the end surface is semi-circular.

5. The breathing assistance apparatus of claim 1, wherein during normal opening and closing movement of the lid, translation of the post within the recess does not occur.

6. The breathing assistance apparatus of claim 5, wherein the guide structure and the cam structure do not interact when the lid is in the attached closed position.

7. The breathing assistance apparatus of claim 1, wherein the second distance is equal to a third distance defined between the mouth and the end surface.

8. The breathing assistance apparatus of claim 7, wherein a fourth distance defined between an engagement surface of the main body and a post center point is equal to the second distance.

9. The breathing assistance apparatus of claim 8, wherein the post is circular in cross-section and comprises the post center point and a post radius around which the lid rotates during normal opening and closing of the lid.

10. The breathing assistance apparatus of claim 9, wherein the post radius is substantially equal to an end surface radius such that the post is positioned against the end surface, in use.

11. The breathing assistance apparatus of claim 1, wherein the axis of the recess is horizontal.

12. The breathing assistance apparatus of claim 1, wherein the mouth is rearwardly facing.

13. The breathing assistance apparatus of claim 1, wherein the support comprises an upper guide portion and a lower guide portion extending between the mouth and the end surface, and the upper guide portion forms a retention surface that contacts the post to retain the lid on the main body in response to forces tending to separate the lid from the main body.

14. The breathing assistance apparatus of claim 1, wherein the cam structure is on the main body and guide structure is on the lid.

\* \* \* \* \*